United States Patent [19]

Wang et al.

[11] Patent Number: 5,385,556
[45] Date of Patent: Jan. 31, 1995

[54] ENDCAP FOR HYPODERMIC SYRINGE

[76] Inventors: I-Wen Wang, 2384 Euclid Heights Blvd., Apt. #305, Cleveland Heights, Ohio 44106; Wei-Ming Wang, 4841 Westchester Dr., Apt. #217, Youngstown, Ohio 44515

[21] Appl. No.: 162,934

[22] Filed: Dec. 8, 1993

[51] Int. Cl.6 ............................................. A61M 5/32
[52] U.S. Cl. ................................... 604/192; 604/263
[58] Field of Search ............... 604/192, 187, 263, 110, 604/198

[56] References Cited

U.S. PATENT DOCUMENTS

| | | |
|---|---|---|
| 2,047,010 | 7/1936 | Dickinson . |
| 2,198,666 | 4/1940 | Gruskin . |
| 2,457,464 | 12/1948 | Grose . |
| 2,708,436 | 5/1955 | Cohen . |
| 2,711,732 | 6/1955 | Solomon . |
| 2,854,976 | 10/1958 | Heydrich ........................ 604/263 X |
| 2,938,238 | 5/1960 | Gewecke et al. . |
| 3,245,567 | 4/1966 | Knight . |
| 3,342,319 | 9/1967 | Faulseit . |
| 3,353,664 | 11/1967 | Armentrout et al. . |
| 3,658,061 | 4/1972 | Hall . |
| 3,889,673 | 6/1975 | Dovey et al. . |
| 3,967,621 | 7/1976 | Schwarz . |
| 4,240,425 | 12/1980 | Akhavi . |
| 4,248,246 | 2/1981 | Ikeda . |
| 4,430,080 | 2/1984 | Pasquini et al. . |
| 4,453,935 | 6/1984 | Newton . |
| 4,659,330 | 4/1987 | Nelson et al. . |
| 5,017,189 | 5/1991 | Boumendil ........................ 604/192 |
| 5,024,326 | 6/1991 | Sandel et al. . |
| 5,037,401 | 8/1991 | DeCamp ............................. 604/192 |
| 5,046,612 | 9/1991 | Mostarda et al. ............... 604/263 X |
| 5,067,944 | 11/1991 | Nichols . |
| 5,092,461 | 3/1992 | Adam . |
| 5,242,421 | 9/1993 | Chan ............................... 604/192 X |

Primary Examiner—John D. Yasko
Attorney, Agent, or Firm—Watts, Hoffmann, Fisher & Heinke Co.

[57] ABSTRACT

An endcap for a hypodermic syringe is disclosed. The endcap is comprised of a sheath and a base section. The sheath, having a proximal and distal end, is hollow and resiliently deformable and has a slit extending substantially the length of the sheath. The proximal end of the sheath is open. The base section is attached to and extends radially outwardly from the periphery of the sheath's proximal end. The base section is disposed opposite of the slit and includes two spaced apart outwardly extending leg supports.

14 Claims, 1 Drawing Sheet

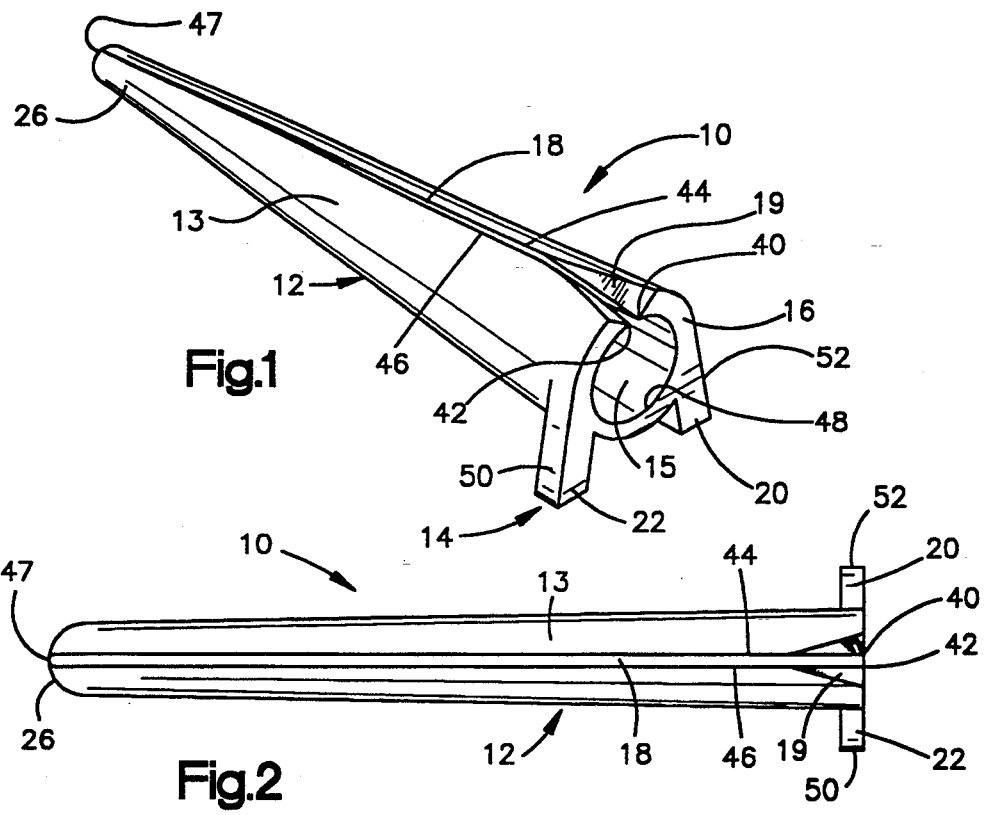
Fig.1
Fig.2
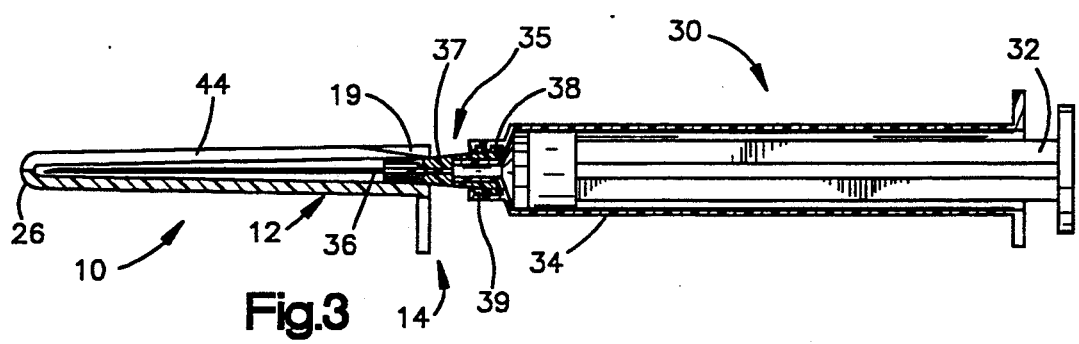
Fig.3
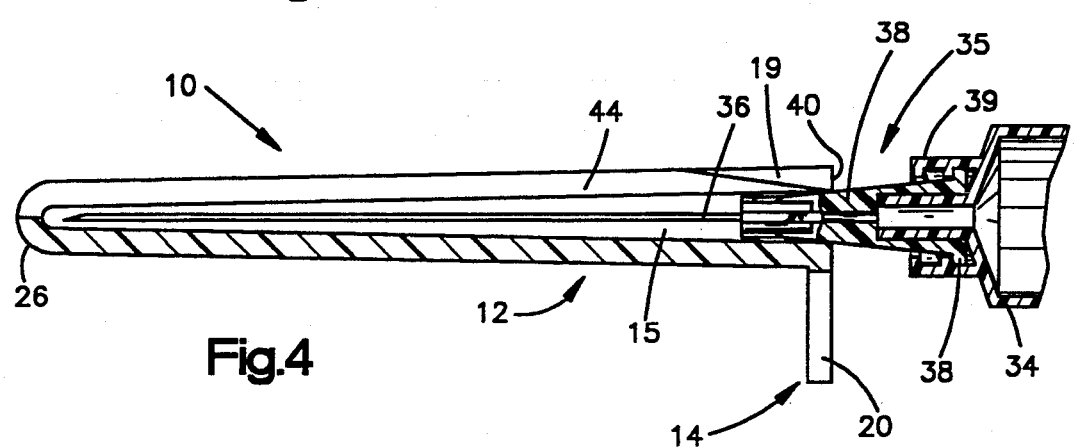
Fig.4

ENDCAP FOR HYPODERMIC SYRINGE

FIELD OF THE INVENTION

This invention relates to protective endcaps or covers for hypodermic syringe needles and, more particularly, protective endcaps allowing for one-handed insertion of the needle into the endcap.

BACKGROUND OF THE INVENTION

After a hypodermic needle has been used to inject medication or extract blood or other body fluids from a patient, the needle is contaminated with the patient's blood and/or body fluids. A medical attendant, if punctured by the used syringe needle, is at risk of being infected by diseases present in the patient's blood and/or body fluid. The insertion of the contaminated needle into a protective endcap renders the needle safe for subsequent handling and/or disposal. However, the medical attendant attempting to insert the contaminated needle into the endcap is exposed to risk of accidental puncture.

Protective endcaps of conventional design require the medical attendant to hold the endcap in one hand and the syringe in the other hand. The attendant must properly align the needle with the open end of the endcap and then insert the needle into the endcap. The open end of the endcap may snap fit or be threaded onto the exterior of the fitting at the base of the needle. Obviously, if the attendant misaligns the needle and the endcap opening when attempting to insert the needle into the endcap, the hand holding the endcap may be punctured. Additionally, even if the needle and the endcap are properly aligned during insertion, there is a risk of the needle piercing the cap and puncturing the attendant's hand.

In an attempt to overcome the risk of accidental puncture inherent with endcaps requiring the use of two hands to linearly insert the needle into the endcap, endcaps allowing for single-handed insertion have been proposed. These devices characteristically have an endcap portion and an attached clamping member. The clamping member slidably attaches to the syringe barrel. The medical attendant holding the syringe may move the clamping member up or down the syringe barrel with one finger thereby advancing or retracting the endcap portion to effectuate encapsulation of the tip of the needle.

Unfortunately, these proposed single-handed endcaps are complex and expensive to manufacture as compared to endcaps requiring two hands to insert. In addition, hypodermic syringes have various barrel diameters depending on the manufacturer and the application. Since the proposed single-handed endcaps do not have adjustable diameter clamping members, different sizes of endcaps would have to be manufactured to correspond to the various hypodermic needle barrel diameters.

SUMMARY OF THE INVENTION

The primary object of this invention is to provide a protective endcap for a hypodermic syringe needle which minimizes the risk of accidental puncture during insertion of the needle into the endcap. Another object of this invention is to provide an endcap permitting one-handed insertion of the needle into the endcap. Yet another object of this invention is to provide an endcap permitting a lateral capping motion wherein the movement of the needle during insertion of the needle into the endcap is perpendicular to the needle's longitudinal axis. Yet another object of this invention is to provide an endcap that is easy and inexpensive to manufacture.

Broadly, the invention comprises a hollow, resiliently deformable sheath and a base section. The sheath has a longitudinal slit extending substantially the length of the sheath. The sheath is open at its proximal end. At its proximal end, the outer surface of the sheath includes a tapered v-shaped groove centered about the longitudinal slit. The v-shaped groove flares open outwardly. The depth of the v-shaped groove is greatest at the proximal end of the sheath and is tapered such that the depth of the groove decreases as the distance from the proximal end of the sheath increases. The base portion is attached to and extends radially outwardly from the periphery of the proximal end of the sheath. The base portion is disposed opposite the longitudinal slit.

To insert the syringe needle into the endcap, the base portion is placed on a horizontal surface. The syringe is positioned above the endcap such that the longitudinal axis of the needle is parallel with the longitudinal axis of the sheath. A base portion of the needle is aligned with the proximal end of the sheath. The syringe is moved downward, the needle base contacts and exerts pressure on the outer surface of the sheath in the region of the v-shaped groove. The pressure of the needle base on the v-shaped groove causes the proximal endpoints of the slit to move apart, thus, spreading the slit open. As the downward movement of the syringe is continued, the needle base spreads the slit's proximal endpoints sufficiently to allow the syringe needle to enter the sheath without contacting the edges of the slit. After the needle base passes through the slit, the slit returns to its original unspread condition. The needle is confined within the sheath. The proximal end of the sheath encircles and exerts pressures on the periphery of the needle base thereby securing the endcap to the syringe via a compressive frictional fit.

BRIEF DESCRIPTION OF THE DRAWINGS

FIG. 1 is a perspective view of the hypodermic syringe needle endcap constructed in accordance with the present invention;

FIG. 2 is a plan view of the endcap of FIG. 1;

FIG. 3 is a sectional view of the endcap of FIG. 1 with a hypodermic syringe needle inserted; and, FIG. 4 is an enlarged sectional view of the endcap and hypodermic syringe of FIG. 3.

DESCRIPTION OF THE PREFERRED EMBODIMENT

As can be seen in FIGS. 1 and 2, the endcap shown generally as 10 is comprised of a sheath section 12 and a base section 14. The sheath 12 is hollow, having an outer surface 13 and an inner surface 15, and is resiliently deformable. In the preferred embodiment, the sheath 12 is generally cone-shaped and comprised of a resilient polymer such as polypropylene. The sheath's proximal end 16 is open. A longitudinal slit 18 extends substantially the length of the sheath. In the region adjacent the sheath's proximal end, a tapered v-shaped groove 19 is notched in the outer surface 13 of the sheath. The v-shaped groove 19 is centered about the longitudinal slit 18 and opens outwardly toward the outer surface 13. The depth of the groove is greatest at the proximal end 16 and decreases as the distance from the proximal end increases. The base section 14 is attached to and extends radially outwardly from the periphery of the sheath's proximal end 16. The base 14 is disposed opposite the slit 18. In the preferred embodiment, the base 14 is comprised of two spaced apart outwardly extending leg supports 20, 22.

As can be seen in FIGS. 3 and 4, a hypodermic syringe 30 is comprised of a plunger 32, a barrel 34 and a needle assembly 35. The needle assembly 35 includes a needle 36, a needle base 37 and a male luer fitting 38 at the proximal end of the needle base 37. The male luer fitting 38 coacts with a syringe female luer fitting 39 extending from a distal end of the syringe barrel 34 to secure the needle assembly 35 to the syringe 30.

To achieve a proper fit between the endcap 10 and the syringe 30, the inner diameter of the sheath's proximal end 16 must be approximately equal to the outer diameter of the needle base 37 thereby permitting a compressive frictional fit of the endcap to the needle base 37. Additionally, the length of longitudinal slit 18 must exceed the length of needle 36.

To insert the syringe needle 36 into the endcap 10, the medical attendant places the endcap 10 on a horizontal surface (not shown) such that the legs 20, 22 are in contact with the surface. This results in the slit 18 facing upwardly. The sheath's distal end 26 also is in contact with the surface thereby providing a third point of support for the endcap 10. The attendant grasps the hypodermic syringe barrel 34 and positions it above the endcap 10 such that the longitudinal axis of the needle is parallel to the longitudinal axis of endcap. The needle base 37 is aligned with the sheath's proximal end 16. The attendant moves the syringe downward toward the endcap 10. The needle base 37 contacts and exerts pressure on the outer surface 13 of the sheath in the area of the v-shaped groove 19. The pressure of the needle base 37 on the outer surface of the sheath causes proximal endpoints 40, 42 of the sheath slit edges 44, 46 to spread apart.

As the downward movement of the syringe 30 continues, the outer diameter of the needle base 37 further spreads the endpoints 40, 42 resulting in the slit 18 opening in a generally triangular configuration. The base or widest portion of the triangular opening being at the sheath's proximal end 16 while the apex 47 of the triangular opening is at the distal end 26 of the sheath. As the needle base 37 passes through the sheath's proximal end 16, the opening of the slit 18 is sufficiently wide to allow needle 36 to enter the hollow interior of sheath 12 without contacting sheath edges 44, 46. When the needle base 37 contacts the bottom 48 of the sheath's proximal end the downward movement of the syringe 30 is stopped and the insertion is complete.

The resilient nature of the sheath 12 causes the sheath to return to its original unspread configuration after the needle base 37 passes through slit 18. This results in the inner surface 15 of the sheath in the region of the proximal end 16 encircling and exerting pressure on the outer surface of the needle base 37. Thus, a compressive friction fit secures the endcap 10 to the needle base 37 and the needle 36 is enclosed within the sheath 12.

The insertion of needle into the sheath is accomplished by the attendant with the use of one hand. During the insertion process the attendant's hand is grasping the syringe barrel and is well removed from the tip of the needle. Additionally, the insertion movement is laterally downward, i.e., perpendicular to the longitudinal axis of the needle, the tip of the needle is never moved in a path that would intersect with the attendant's body. Thus, the risk of accidental puncture of the attendant is minimized. Additionally, if desired, the encapsulated needle can be removed from the syringe 30. By firmly grasping the sheath 12 near its proximal end 16 and appropriately rotating the endcap 10 together with the underlying needle base 37, the needle male luer fitting 38 would "unscrew" from the syringe female luer fitting 39 thereby separating the needle 36 from the syringe 30.

Alternatively, instead of moving the syringe 30 to the stationary endcap 10 disposed on the horizontal surface, the position of the endcap 10 and syringe 30 may be reversed with the syringe 30 being placed on the horizontal surface and the endcap 10 moved to the syringe 30. The attendant grasps the endcap's legs 20, 22 with one hand and positions the endcap 10 above the syringe 30 such that the longitudinal axis of the endcap is parallel with the longitudinal axis of the needle and the sheath's proximal end 16 is aligned with the needle base 37. The attendant places his other hand on the syringe barrel 34 to prevent the syringe 30 from moving when the endcap 10 is brought into contact with needle base 37. The endcap 10 is moved downward toward the syringe 30. The outer surface 13 of the sheath in the region of the v-shaped groove 19 contacts the needle base 37. The needle base 37 exerts pressure on the outer surface of the sheath and causes sheath edge proximal end points 40, 42 to spread apart. The attendant may facilitate the spreading of slit 18 by applying pressure to outer leg surfaces 50, 52. As the attendant continues to move the endcap 10 downward, the outer diameter of the needle base 37 further spreads the end portions 40, 42 resulting in the slit opening in a triangular configuration as described previously. When the bottom 48 of the sheath's proximal end contacts the needle base 37, the downward movement of the endcap 10 is stopped and the insertion is complete.

A third method of encapsulating the syringe needle 36 within the sheath 12 involves grasping the syringe barrel 34 in one hand and grasping the base 14 of the endcap with the other hand. Using a motion which is perpendicular with respect to the longitudinal axis of the needle 36, the needle is inserted into the sheath in the manner described previously. Pressure is applied to the outer legs 50, 52 of the base to facilitate the spreading of slit 18. Since the insertion motion is perpendicular to the longitudinal axis of the needle, the potential danger of needle stick injury is minimized.

To remove the syringe 30 from the endcap 10, the medical attendant merely grasps the distal end 26 of the endcap and the syringe barrel 34 and pulls the two in opposite directions.

As an alternate embodiment, the endcap 10 may be designed such that the endcap's proximal end 16 encircles and grips the syringe barrel 34 as opposed to the needle base 37. However, since the sizes of the needle bases tend to be more standardized than the size of syringe barrels, fewer sizes of endcaps need to be manufactured and stocked in inventory if needle base encircling endcaps are used.

While the preferred embodiment for practicing the present invention has been described in detail, it will be apparent that various modifications or alterations may be made therein without departing from the spirit and scope of the invention, set forth in the appended claims.

We claim:

1. An endcap for a syringe including a needle, the endcap comprising;
   a. a hollow, resiliently deformable sheath having:
      (i) an open slit extending substantially the length of said sheath and terminating at a proximal end of said sheath, said slit having a substantially uniform slit width;
      (ii) an open proximal end having a periphery adapted to encircle and compressively attach to such syringe; and,
   b. a base section attached to and extending radially outwardly from a portion of said periphery of said proximal end, said base section being disposed opposite said slit whereby said proximal end of said sheath is supported by said base section such that said slit faces upwardly when said base section is disposed on a support surface.

2. The endcap of claim 1 wherein said sheath is generally cone-shaped.

3. The endcap of claim 1 wherein said base section includes two spaced apart outwardly extending leg supports.

4. The endcap of claim 1 wherein said sheath is comprised of polypropylene.

5. An endcap for a syringe needle comprising:
   a. a hollow, resiliently deformable sheath having:
      (i) a slit extending substantially the length of said sheath;
      (ii) the sheath having a proximal end and a distal end, and an inner and outer surface, said proximal end being open and having a periphery and wherein said outer surface of said sheath includes a tapered v-shaped groove adjacent said proximal end of said sheath, said groove being centered about said slit and opening outwardly toward said outer surface, and said groove further having a depth which decreases with increasing distance from said proximal end of said sheath; and
   b. a base section attached to and extending radially outwardly form said periphery of said proximal end, said base section being disposed opposite said slit.

6. A method of inserting a needle of a syringe into an endcap, said syringe comprising a hollow syringe barrel including a fitting at a distal end of said barrel, a plunger insertable in said barrel, and a needle assembly, said needle assembly including a needle, a needle base and a needle fitting at the proximal end of the needle assembly, said needle fitting adapted to coact with said syringe barrel fitting to removably secure said needle assembly to said syringe barrel, said needle base having an outer diameter, said endcap comprising a hollow, resiliently deformable sheath having a proximal and distal end and longitudinal slit extending substantially the length of the sheath, the length of said slit exceeding the length of said needle and an open proximal end, said proximal end having an inner diameter substantially equal to said outer diameter of said needle base, a tapered, outwardly opening v-shaped groove adjacent said proximal end, said groove centered about said slit, and a base section attached to and extending radially outwardly from the periphery of the proximal end of the sheath and being disposed opposite of the slit, the steps of the method comprising:
   a. positioning said endcap on a support surface such that said base section is in contact with said surface and said slit is upwardly facing;
   b. grasping said syringe barrel and positioning said syringe above said endcap such that a longitudinal axis of said needle is parallel to a longitudinal axis of the endcap;
   c. aligning said needle base with said sheath's v-shaped groove; and,
   d. moving said syringe vertically downward so that said needle base passes through said slit at said sheath's proximal end and said proximal end of said sheath encircles and is compressively attached to said outer diameter of said needle base.

7. In combination, a syringe and an endcap, said syringe comprising a needle assembly and a syringe barrel, said needle assembly including a needle and a needle base portion and a fitting at a proximal end of said assembly, said fitting coacting with a syringe fitting disposed at a distal end of said syringe barrel to removably attach said needle assembly to said syringe barrel, said needle base portion having an outer diameter, and said endcap comprising:
   a. a hollow, resiliently deformable sheath having:
      (i) a proximal end and a distal end and an inner and outer surface, said proximal end being open and having an inner diameter substantially equal to said outer diameter of said needle base;
      (ii) an open slit extending substantially the length of the sheath terminating at the proximal end of the sheath and having a substantially uniform slit width; and,
   b. a base section attached to and extending radially outwardly from the periphery of said proximal end whereby said proximal end of said sheath is supported by said base section such that said slit faces upwardly when said base section is disposed on a support surface, said base section being disposed opposite said slit, wherein said sheath encapsulates said needle and said proximal end of said sheath encircling and compressively engaging the outer diameter of said needle base.

8. The combination syringe and endcap of claim 7 wherein said endcap sheath is generally cone-shaped.

9. The combination syringe and endcap of claim 7 wherein said endcap base section includes two spaced apart outwardly extending leg supports.

10. The combination syringe and endcap of claim 7 wherein said endcap sheath is comprised of polypropylene.

11. In combination, a syringe and an endcap, said syringe comprising a needle assembly and a hollow cylindrical barrel, said barrel having an outer diameter, said needle assembly including a needle, a needle base and a fitting at a proximal end of said assembly, said fitting coacting with a syringe fitting disposed at a distal end of said syringe barrel for attachment of said needle assembly to said syringe barrel, and said endcap comprising:
   a. a hollow, resiliently deformable sheath having:
      (i) a proximal end and a distal end and an inner and outer surface, said proximal end being open and having an inner diameter substantially equal to said outer diameter of said syringe barrel;
      (ii) an open slit extending substantially the length of the sheath terminating at the proximal end of the sheath and having a substantially uniform slit width; and
   b. a base section attached to and extending radially outwardly from the periphery of said proximal end, said base section being disposed opposite said slit whereby said proximal end of said sheath is supported by said base section such that said slit faces upwardly when said base section is disposed on a support surface, wherein said sheath encapsulates said needle and said proximal end of said sheath encircling and being compressively attached to the outer diameter of said syringe barrel.

12. The combination syringe and endcap of claim 11 wherein said endcap sheath is generally cone-shaped.

13. The combination syringe and endcap of claim 11 wherein said endcap base section includes two spaced apart outwardly extending leg supports.

14. The combination syringe and endcap of claim 11 wherein said endcap sheath is comprised of polypropylene.

* * * * *